United States Patent
Mohrholz et al.

(10) Patent No.: US 8,542,273 B2
(45) Date of Patent: Sep. 24, 2013

(54) ARRANGEMENT AND METHOD FOR GENERATING IMAGES WITH EXPANDED DYNAMICS

(75) Inventors: Uwe Mohrholz, Jena (DE); Frank Teige, Jena (DE); Detlef Biernat, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 448 days.

(21) Appl. No.: 12/680,146

(22) PCT Filed: Sep. 20, 2008

(86) PCT No.: PCT/EP2008/007952
§ 371 (c)(1),
(2), (4) Date: Mar. 25, 2010

(87) PCT Pub. No.: WO2009/043494
PCT Pub. Date: Apr. 9, 2009

(65) Prior Publication Data
US 2010/0201799 A1 Aug. 12, 2010

(30) Foreign Application Priority Data
Sep. 27, 2007 (DE) .......................... 10 2007 046 210

(51) Int. Cl.
*H04N 7/18* (2006.01)
*A61B 3/14* (2006.01)

(52) U.S. Cl.
USPC ............................................. 348/78; 351/214

(58) Field of Classification Search
None
See application file for complete search history.

(56) References Cited

U.S. PATENT DOCUMENTS

| 4,584,606 | A | | 4/1986 | Nagasaki |
| 5,141,302 | A | * | 8/1992 | Arai et al. ..................... 351/205 |
| 5,638,119 | A | | 6/1997 | Cornuejols |
| 5,801,773 | A | | 9/1998 | Ikeda |
| 5,993,001 | A | * | 11/1999 | Bursell et al. ................. 351/212 |
| 6,204,881 | B1 | * | 3/2001 | Ikeda et al. ................... 348/362 |
| 8,109,634 | B2 | * | 2/2012 | Gil ................................. 351/206 |
| 8,126,246 | B2 | * | 2/2012 | Farrer et al. ................... 382/131 |
| 2009/0046248 | A1 | * | 2/2009 | Niven ............................ 351/206 |

FOREIGN PATENT DOCUMENTS

| DE | 34 32 229 | | 5/1985 |
| DE | 37 34957 | | 5/1988 |
| EP | 0 545 528 | | 6/1993 |
| EP | 1 271 935 | | 1/2003 |
| EP | 1 761 071 | | 3/2007 |
| WO | WO 00/21432 | * | 4/2000 |

OTHER PUBLICATIONS

Notification of Transmittal of Translation of the International Preliminary Report on Patentability dated Apr. 29, 2010; The International Bureau of WIPO, 1211 Geneva 20, Switzerland.

(Continued)

*Primary Examiner* — Gims Philippe
*Assistant Examiner* — Reza Aghevli
(74) *Attorney, Agent, or Firm* — Frommer Lawrence & Haug LLP

(57) ABSTRACT

An ophthalmic device and an arrangement for generating images with expanded dynamic range and a corresponding method for generating images with expanded dynamic range have at least one beamsplitter, in particular with an asymmetric splitting ratio, and at least two image sensors, wherein the image sensors are reflected into a common imaging beam path by the at least one beamsplitter.

15 Claims, 2 Drawing Sheets

(56) References Cited

OTHER PUBLICATIONS

Patent Abstract of Japan; Publication No. 08223494; Publication Date Aug. 30, 1996.
Patent Abstract of Japan; Publication No. 2002372696; Publication Date Dec. 26, 2002.
Patent Abstract of Japan; Publication No. 08223491; Publication Date Aug. 30, 1996.

* cited by examiner

ARRANGEMENT AND METHOD FOR GENERATING IMAGES WITH EXPANDED DYNAMICS

The present application claims priority from PCT Patent Application No. PCT/EP2008/007952 filed on Sep. 20, 2008, which claims priority from German Patent Application No. 10 2007 046 210.9 filed on Sep. 27, 2007, the disclosure of which is incorporated herein by reference in its entirety.

BACKGROUND OF THE INVENTION

1. Field of the Invention

The invention is directed to an ophthalmic device and an arrangement for generating images with expanded dynamic range and to a corresponding method for generating images with expanded dynamic range.

2. Description of Related Art

In the following, the expression 'radiant energy' is understood to mean not the energy of individual photons, but rather the total energy of all photons which is integrated over an exposure time.

The dynamic range of an image indicates the ratio of the highest intensity and lowest intensity contained in the image. When making a photographic recording of an object, either a short exposure time (low radiant energy) must be selected for discernible imaging of bright areas without saturation effects (to prevent overexposure) or a long exposure time (high radiant energy) must be selected in order to image dark areas with sufficient contrast (to prevent underexposure). The other areas are then necessarily underexposed or overexposed in the recorded image. In both cases, the dynamic range is low. A known solution to this problem is to record two or more images of the same object successively with different exposure times. The bright areas of the object and the dark areas of the object are then discernible to varying degrees in the different images. These different images must be viewed in parallel in order to perceive all of the information.

Numerous methods are known in the art for combining a plurality of photographic images of low dynamic range, particularly digital photographs, to form an individual image with an expanded dynamic range. Bright areas and dark areas can then be perceived simultaneously in the combined image with expanded dynamic range.

Particularly in ophthalmology when imaging segments of the eye, weakly reflective structures and highly reflective structures occur at close distances from one another. For a more accurate diagnosis, all of the structures must be imaged as distinctly as possible, preferably within an individual image with a high dynamic range so as to perceive all of the structures simultaneously. However, sequential imaging with different exposure times on the eye is unacceptable for two reasons. First, the eye is constantly in motion, which typically results in the eye being recorded in different positions. An individual image with expanded dynamic range can be compiled from different individual recordings of this kind only with great effort. Second, a repeated exposure with the necessary intensive illumination means, in effect, a longer exposure and, therefore, a larger dose of energy deposited in the eye because a large proportion of the light falling on the eye is absorbed in the eye. However, the deposition of energy should be kept as small as possible in order to minimize the risk of damage to health.

SUMMARY OF THE INVENTION

Therefore, it is the object of the invention to improve an ophthalmic device and an arrangement and a method of the type mentioned above in such a way that an image of the object can be determined with an expanded dynamic range with low radiation loading of an object to be recorded and with little motion blur.

This object is met by an ophthalmic device and an arrangement having the features indicated in claim 1 and claim 2 and by a method having the features indicated in claim 12.

Advantageous embodiments of the invention are indicated in the respective dependent claims.

According to the invention, at least one beamsplitter and at least two image sensors are provided for an ophthalmic device for generating images with expanded dynamic range, particularly a fundus camera for imaging the fundus of the eye or a slit lamp, wherein the image sensors are reflected into a common imaging beam path by the at least one beamsplitter. Splitter mirrors, splitter prisms and optical gratings in particular can be used as beamsplitters.

By aligning the image sensors in a common beam path, a plurality of images can be recorded with an identical scene content and identical motion blur. Combining to form a total image with expanded dynamic range is made particularly simple in that the imaged scene content in the image sensors is identical. The identical motion blur in the individual images results in a minimal motion blur in the total image. This is particularly advantageous in ophthalmology because of the continual involuntary eye movements. In addition, no multiple exposures are required because of the parallel image recording. The radiation loading of the eye in the form of energy deposition can be minimized in this way.

Accordingly, in the method according to the invention for generating images with an expanded dynamic range by means of an ophthalmic device, particularly a fundus camera or a slit lamp, the image sensors are reflected into a common imaging beam path by the at least one beamsplitter, and individual images are recorded with different radiant energies by the image sensors, and a total image with expanded dynamic range is generated from these individual images.

Arrangements which record a plurality of images with different radiant energies simultaneously or at least in an overlapping manner with respect to time by using a plurality of image sensors are known in the art. For example, U.S. Pat. No. 5,801,773 describes an image processing device having a plurality of image sensors and a beamsplitter which reflects the image sensors and the color filters, optical lowpass filters and neutral density filters preceding them into a common imaging beam path. The image sensors record individual images with different radiant energies. The different radiant energies are achieved through the neutral density filters preceding the image sensors or, alternatively, through different exposure times of the image sensors. The individual images are then combined to form a total image with expanded dynamic range.

The radiant energy transmitted to the image sensors is appreciably reduced through the combined use of optical lowpass filters, color filters and neutral density filters. In order to compensate, the intensity and/or duration of the illumination and exposure must be increased if a sufficient contrast is to be achieved. This not only shortens the life of the light sources, but also means an increased radiation load for the object to be recorded. This is unacceptable especially for ophthalmic recordings, since the radiation loading of the eye would be too high. Therefore, the known arrangement is not usable for ophthalmological applications. In addition to the increased illumination intensity owing to the lowpass filters and color filters, the use of different exposure times as an alternative to neutral density filters results in the further disadvantage of differing motion blurs and the risk of differing recorded areas, which has a significantly adverse effect on a total image with expanded dynamic range particularly for ophthalmic recordings because of rapid eye movements. In addition, complicated controlling means are required for different exposure times.

According to the invention, arrangements for generating images with expanded dynamic range can be improved by at least one beamsplitter and at least two image sensors in that at least one beamsplitter has an asymmetric or asymmetrically adjustable splitting ratio. In this case, too, the image sensors are reflected into a common imaging beam path by the at least one beamsplitter. Beamsplitters with adjustable splitting ratios are known in the art.

A splitter mirror with an asymmetric or asymmetrically adjustable splitting ratio makes it possible to record different radiant energies in a plurality of images simultaneously, but without disadvantageous absorption of light through neutral density filters on the one hand and without complicated controlling means for different exposure times on the other hand. Different radiant energies in the reflected and transmitted light are made possible in an economical manner by the asymmetric splitting ratio. Since no light is absorbed in filters, the arrangement can make full use of the radiant energy reflected at the object to be recorded. The illumination intensity and/or illumination period can be minimized in this way.

Accordingly, in the method according to the invention for generating images with expanded dynamic range by means of an arrangement with at least one beamsplitter with an asymmetric or asymmetrically adjustable splitting ratio and at least two image sensors, the image sensors are reflected by the at least one beamsplitter into a common imaging beam path and individual images with different radiant energies are recorded simultaneously and with identical exposure times by the image sensors, and a total image with expanded dynamic range is determined therefrom.

Particularly the final beamsplitter in the imaging beam path preferably has an asymmetric or asymmetrically adjustable splitting ratio. In the event that more than one beamsplitter is provided, the rest of the beamsplitters can have, in particular, a splitting ratio of 50:50 so that the incident light in the imaging beam path is reflected out in a cascading manner at every beamsplitter and 50% of the remaining light is reflected out in the respective image sensor. However, all of the beamsplitters can also be constructed asymmetrically.

In an advantageous manner, a control unit is provided which records individual images with different radiant energies by means of the image sensors and generates a total image with expanded dynamic range from the individual images. Accordingly, the image with expanded dynamic range can be observed directly at the recording arrangement. Alternatively or in addition, the control unit can make the individual images available at an interface. In this way, external computers can be used to determine the total image. These external computers can have greater computing capacity because their structural dimensions are unlimited in principle. Therefore, more complex algorithms can be used to expand the dynamic range.

The control unit advisably records the individual images so as to overlap in time. This reduces the illumination period compared to a strictly sequential recording of individual images.

Embodiments in which the control unit records all of the individual images with identical exposure time simultaneously are particularly preferred. This allows a minimal illumination period with minimal radiation loading of the object to be recorded.

The image sensors preferably have an identical imaging scale and pixel-identical orientation. Accordingly, the total image can be determined with a minimum of effort by exclusively pixel-based selection operations.

In an advantageous manner, every beamsplitter is a neutral splitter with respect to the light color of the illumination employed. When illuminating with light of a plurality of wavelengths, particularly with white light, this enables an identical color distribution in all of the individual images.

In preferable embodiment forms, the beam path segments between each of the image sensors and the beamsplitter which reflects the respective image sensor into the imaging beam path are formed without filters. The absolute radiant energy received in the image sensors is reduced by filters of any kind, particularly for adjusting predetermined contrasts in the individual images. This, in turn, increases radiation loading at a given contrast to be achieved owing to more intensive illumination. According to the invention, filters can be dispensed with because the different contrast ratios are achieved by the asymmetric splitting ratio of the at least one beamsplitter.

The arrangement according to the invention is advantageously used in an ophthalmic device, particularly in a mydriatic or non-mydriatic fundus camera or a slit lamp.

DETAILED DESCRIPTION OF EMBODIMENTS

It is to be understood that the figures and descriptions of the present invention have been simplified to illustrate elements that are relevant for a clear understanding of the present invention, while eliminating, for purposes of clarity, many other elements which are conventional in this art. Those of ordinary skill in the art will recognize that other elements are desirable for implementing the present invention. However, because such elements are well known in the art, and because they do not facilitate a better understanding of the present invention, a discussion of such elements is not provided herein.

The present invention will now be described in detail on the basis of exemplary embodiments. Corresponding parts have the same reference numbers in all of the drawings.

Figure 1:
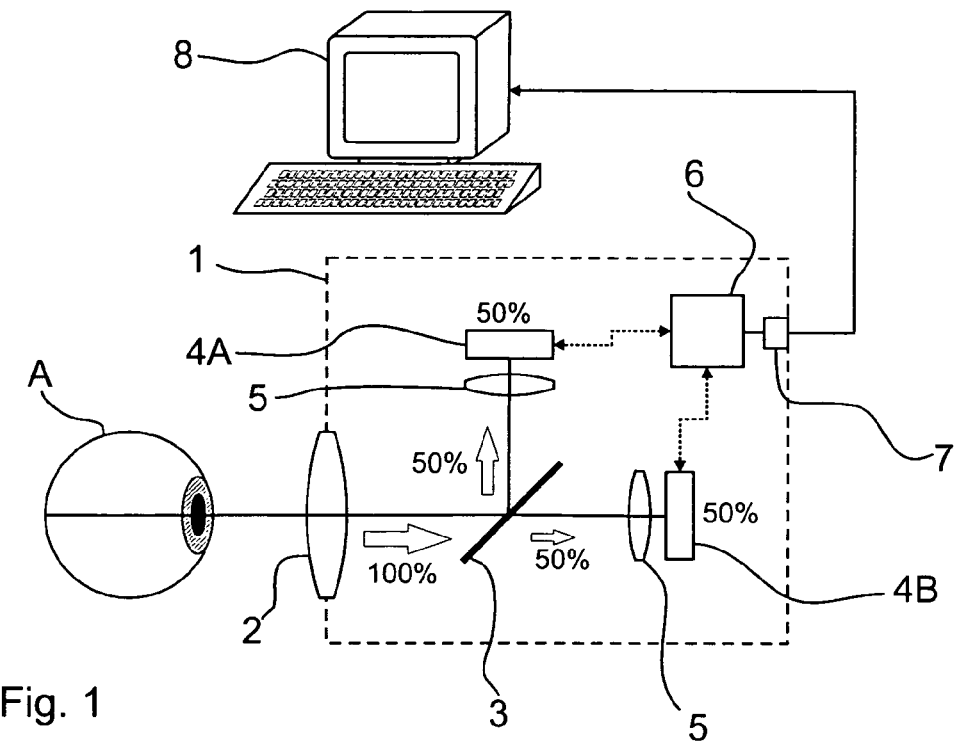
FIG. 1 shows an imaging beam path of a first high dynamic range fundus camera.

As arrangement 1, a first fundus camera for recording the retina R of the eye A is shown schematically in FIG. 1. The fundus camera can be designed for mydriatic or non-mydriatic operation. In alternative constructions (not shown), the arrangement 1 can be constructed as a slit lamp or as a photographic apparatus.

The simplest form of the arrangement 1 according to the invention is realized in the illustrated embodiment form as fundus camera. It comprises, in an imaging beam path, an objective 2, a beamsplitter 3, and two image sensors 4A/4B preceded by optics 5, and a control unit 6. The illumination beam path with light source comprising, e.g., high-power light-emitting diodes is not shown. The arrangement 1 is connected to an external computer 8 by an interface 7, e.g., a serial bus.

The beamsplitter 3 is constructed as a neutral splitter mirror with a symmetrical splitting ratio of 50:50 (reflection to transmission). Accordingly, half of the light impinging from the eye A through the objective 2 is directed to the first image sensor 4A and half is directed to the second image sensor 4B. The relative proportions of radiant energy are indicated at the arrows in the beam path. The resulting absolute proportions of the radiant energy incident in the objective 2 are indicated at the image sensors 4.

The control unit 6 serves, on the one hand, to adjust the exposure times of the image sensors 4 asymmetrically for recording the individual images. On the other hand, it reads out the individual images from the image sensors 4 after these individual images have been recorded and sends them to the external computer 8 via the interface 7. The external computer 8 monitors and controls the control unit 6. It provides the control unit 6 directly with the exposure times for the image sensors 4 or, indirectly, with ratios between the respective radiant energies to be recorded. In the latter case, the control unit 6 determines the necessary exposure times of the image sensors 4 from the given energy ratios. The external computer 8 initiates the time-overlapping recording of the individual images by means of the control unit 6. In this connection, the two different exposure time periods of the image sensors 4 can either start simultaneously or end simultaneously. However, the exposure time of one image sensor 4A/B can also start after the beginning of the exposure period of the other respective image sensor 4B/A and can end before the end of this exposure period.

After the individual images have been sent to the external computer 8 via the interface 7, the external computer 8 calculates a total image with high dynamic range from the individual images with low dynamic range by means of algorithms, known per se, for dynamic expansion and displays it on its display. Alternatively or in addition, the total image can be stored on a storage medium, for example, a computer memory or a fixed disk, or sent to a printer.

In an alternative embodiment form (not shown), the internal control unit 6 of the arrangement 1 can be set up for determining the total image with high dynamic range. In this case, only the total image, instead of the individual images, is sent to the external computer 8 via the interface 7. Alternatively or in addition to a connection for an external computer 8, an interface 7 can be designed as a video interface for direct connection of a display device for displaying the total image determined in the control unit 6.

Figure 2:
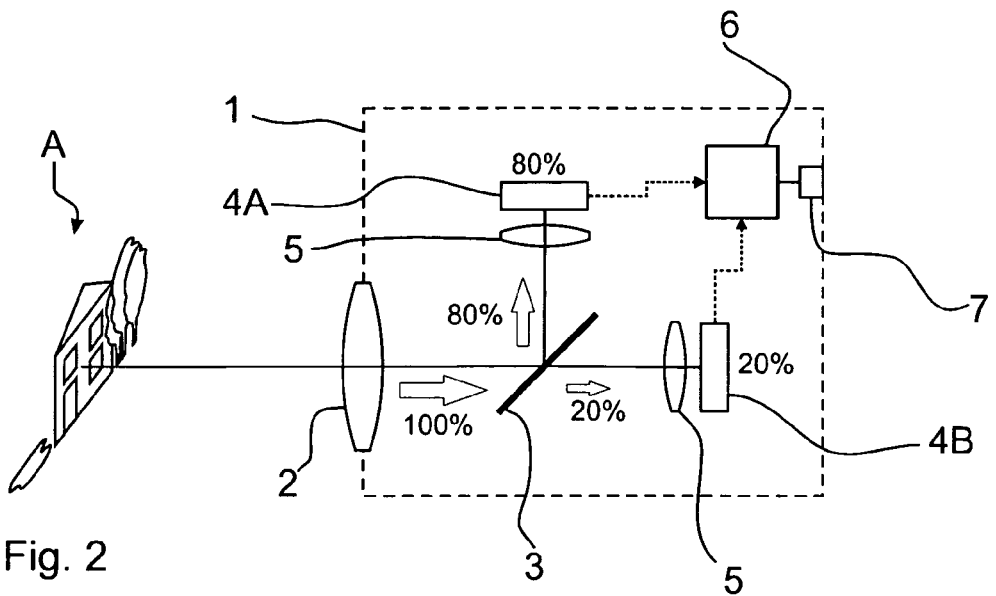
FIG. 2 shows an imaging beam path of a high dynamic range photographic apparatus.

FIG. 2 shows a digital photographic apparatus as arrangement 1 for imaging an object A in a plurality of individual images with a low dynamic range. The arrangement 1 comprises, in an imaging beam path, an objective 2, a beamsplitter 3 and two image sensors 4A/4B preceded by optics 5, and a control unit 6. The photographic apparatus can be outfitted with a flash device as light source (not shown). The arrangement 1 is outfitted with an interface 7 to which an external computer 8 can be connected.

The beamsplitter 3, which is constructed as a splitter prism, has a fixed asymmetric splitting ratio of 80:20 (reflection to transmission). Accordingly, 80% of the light from the object A impinging through the objective 2 is directed to the first image sensor 4A and 20% of this light is directed to the second, or final, image sensor 4B. The relative proportions of radiant energy are indicated at the arrows in the beam path. The resulting absolute proportions of the radiant energy incident in the objective 2 are indicated at the image sensors 4.

The control unit 6 serves exclusively to initiate the recording of the individual images in the image sensors 4 and subsequently to read out the individual images from the image sensors 4, save them in a storage (not shown), and send them to the external interface 7 on demand. The control unit 6 of a photographic apparatus is typically not powerful enough to calculate a total image with expanded dynamic range from the individual images.

In an alternative embodiment form (not shown), the splitting ratio of the beamsplitter 3 can be adjusted in a continuously asymmetric manner. To this end, the control unit 6 is connected to the beamsplitter 3. The splitting ratio can be adjusted at the photographic apparatus either directly or indirectly by specifying the ratio between the radiant energies of the image sensors 4 which is to be achieved.

Figure 3:
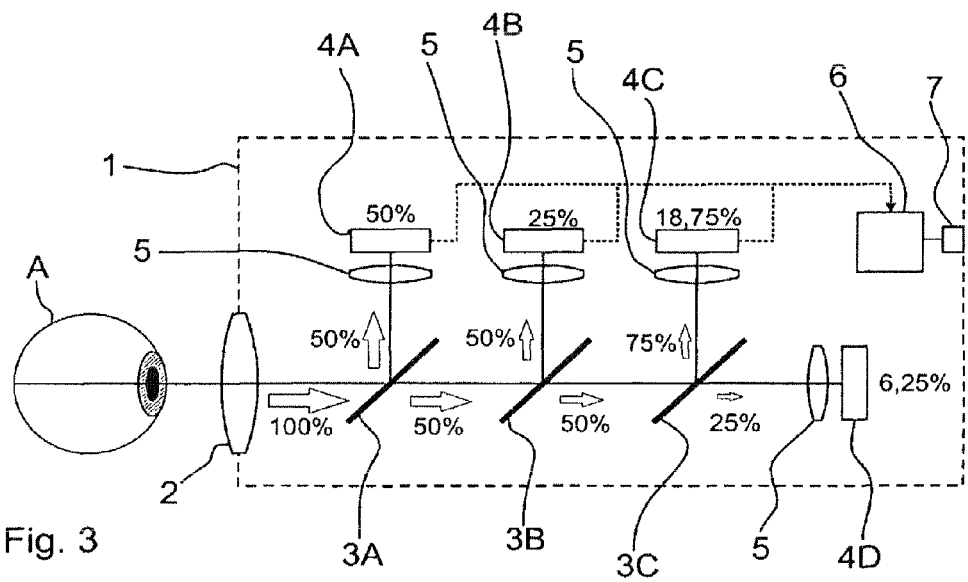
FIG. 3 shows an imaging beam path of a second high dynamic range fundus camera.
Figure 4:
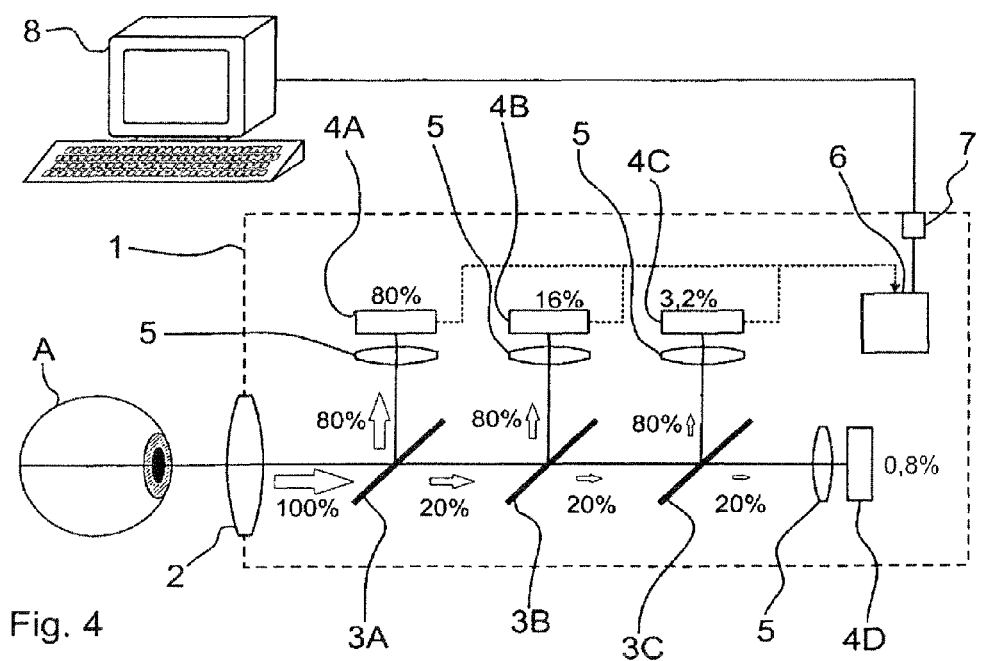
FIG. 4 shows an imaging beam path of a third high dynamic range fundus camera.

FIG. 3 shows a schematic illustration of a second fundus camera for recording the retina R of the eye A as arrangement 1. The fundus camera can be designed for mydriatic or non-mydriatic operation. The alternative construction as slit lamp or as photographic apparatus is possible (not shown).

The arrangement 1 comprises, in an imaging beam path, an objective 2, three beamsplitters 3A/3B/3C and four image sensors 4A/4B/4C/4D preceded by optics 5, and a control unit 6. The illumination beam path with light source is not shown. The arrangement 1 can be connected by an interface 7 to an external computer 8.

The first and second beamsplitters 3A, 3B are designed as neutral splitter mirrors with a symmetric splitting ratio of 50:50. The final beamsplitter 3C is a neutral splitter mirror with a fixed asymmetric splitting ratio of 75:25. Accordingly, half of the light impinging from the eye A through the objective 2 is directed to the first image sensor 4A and half is directed to the second beamsplitter 3B. Half of the incident light from the latter is directed to the second image sensor 4B and half is directed to the third beamsplitter 3B. Of the incident light from the latter, 75% is directed to the third image sensor 4C and 25% is directed to the fourth, and final, image sensor 4D. The relative proportions of radiant energy are indicated at the arrows in the beam path. The resulting absolute proportions of the radiant energy incident in the objective 2 are indicated at the image sensors 4.

After the recording, the control unit 6 reads out the individual images from the image sensors 4 and sends them to the external computer 8 via the interface 7. The external computer 8 monitors and controls the control unit 6. It provides the control unit 6 directly with the exposure times for the image sensors 4 or, indirectly, with ratios between the respective radiant energies to be recorded. In the latter case, the control unit 6 determines the necessary exposure times of the image sensors 4 from the given energy ratios. The external computer 8 initiates the time-overlapping recording of the individual images by means of the control unit 6. The two different exposure time periods of the image sensors 4 can either start simultaneously or end simultaneously. However, the exposure time of one image sensor 4A/B can also start after the beginning of the exposure period of the other respective image sensor 4B/A and can end before the end of this exposure period.

After the individual images have been sent to the external computer 8 via the interface 7, the external computer 8 calculates a total image with high dynamic range from the individual images with low dynamic range by means of algorithms for dynamic expansion, known per se, and displays it on its display. Alternatively or in addition, the total image can be stored on a storage medium, for example, a computer memory or a fixed disk, or sent to a printer.

All of the features of all of the embodiment forms described above can be combined with the other embodiment forms.

While this invention has been described in conjunction with the specific embodiments outlined above, it is evident that many alternatives, modifications, and variations will be apparent to those skilled in the art. Accordingly, the preferred embodiments of the invention as set forth above are intended to be illustrative, not limiting. Various changes may be made without departing from the spirit and scope of the inventions as defined in the following claims.

Reference Numbers
1 arrangement
2 objective
3 beamsplitter
4 image sensor
5 optics
6 control unit
7 interface
8 external computer

The invention claimed is:

1. An ophthalmic apparatus for generating an image with expanded dynamic range:
comprising at least one beamsplitter; and
at least two image sensors;
wherein the image sensors are reflected into a common imaging beam path by the at least one beamsplitter; and
wherein the apparatus is an ophthalmic device.

2. The ophthalmic apparatus according to claim 1;
wherein the image sensors are reflected into a common imaging beam path by the at least one beamsplitter;
wherein at least one beamsplitter has an asymmetric or asymmetrically adjustable splitting ratio.

3. The ophthalmic apparatus according to claims 2;
wherein the final beamsplitter in the imaging beam path has an asymmetric or asymmetrically adjustable splitting ratio.

4. The ophthalmic apparatus according to claim 1;
wherein a control unit which records individual images with different radiant energies by means of the image sensors and generates a total image with expanded dynamic range from the individual images.

5. The ophthalmic apparatus according to claim 4;
wherein the control unit records the individual images in an overlapping manner with respect to time.

6. The ophthalmic apparatus according to claim 4;
wherein the control unit records all of the individual images simultaneously with identical exposure time.

7. The ophthalmic apparatus according to claim 1;
wherein the image sensors have an identical imaging scale and have pixel-identical orientation.

8. The ophthalmic apparatus according to claim 1;
wherein every beamsplitter is a neutral splitter with respect to the light color.

9. The ophthalmic apparatus according claim 1;
wherein the beam path segments between each of the image sensors and the beamsplitter which reflects the respective image sensor into the imaging beam path are formed without filters.

10. The ophthalmic apparatus according to claim 1;
wherein the apparatus is a mydriatic or non-mydriatic fundus camera or a slit lamp.

11. A method for generating images with expanded dynamic range by means of an ophthalmic device comprising at least one beamsplitter and at least two image sensors, wherein the image sensors are reflected into a common imaging beam path by the at least one beamsplitter and the following steps are carried out, comprising the steps of:
recording individual images with different radiant energies by means of the image sensors; and
generating a total image with expanded dynamic range from the individual images.

12. The method according to claim 11;
wherein the individual images with different radiant energies are recorded by means of the image sensors simultaneously and with identical exposure times.

13. The method according to claims 12;
wherein an ophthalmic device is used the apparatus with asymmetric beamsplitter and image sensors.

14. The method according to claims 13;
wherein a mydriatic or non-mydriatic fundus camera or a slit lamp is used as the ophthalmic device.

15. A non-transitory computer-readable medium for storing a computer program for generating images with expanded dynamic range by means of an ophthalmic device comprising at least one beamsplitter and at least two image sensors, wherein the image sensors are reflected into a common imaging beam path by the at least one beamsplitter and the following steps are carried out, the computer program performing the steps of:
recording individual images with different radiant energies by means of the image sensors; and
generating a total image with expanded dynamic range from the individual images.

* * * * *